US009975912B2

(12) United States Patent
Dufour et al.

(10) Patent No.: US 9,975,912 B2
(45) Date of Patent: May 22, 2018

(54) METHOD FOR PRODUCING (E,Z)-7,9-DODECADIENYL-1-ACETATE

(71) Applicant: MELCHIOR MATERIAL AND LIFE SCIENCE FRANCE, Lacq (FR)

(72) Inventors: Samuel Dufour, Orthez (FR); Olivier Guerret, Pern (FR)

(73) Assignee: MELCHIOR MATERIAL AND LIFE SCIENCE FRANCE, Lacq (FR)

(*) Notice: Subject to any disclaimer, the term of this patent is extended or adjusted under 35 U.S.C. 154(b) by 0 days. days.

(21) Appl. No.: 15/323,287

(22) PCT Filed: Jul. 2, 2015

(86) PCT No.: PCT/EP2015/065152
§ 371 (c)(1),
(2) Date: Dec. 30, 2016

(87) PCT Pub. No.: WO2016/001383
PCT Pub. Date: Jan. 7, 2016

(65) Prior Publication Data
US 2017/0137447 A1    May 18, 2017

(30) Foreign Application Priority Data
Jul. 2, 2014    (FR) ...................... 14 56322

(51) Int. Cl.
*C07F 9/40* (2006.01)
*C07C 67/08* (2006.01)

(52) U.S. Cl.
CPC ............ *C07F 9/4015* (2013.01); *C07C 67/08* (2013.01)

(58) Field of Classification Search
CPC .............................. C07F 9/4015; C07C 67/08
See application file for complete search history.

(56) References Cited

U.S. PATENT DOCUMENTS

| 3,845,108 | A | 10/1974 | Roelofs et al. |
| 3,954,818 | A | 5/1976 | Labovitz et al. |
| 4,912,253 | A | 3/1990 | Fukumoto et al. |
| 7,932,410 | B2 | 4/2011 | Bedoukian et al. |

FOREIGN PATENT DOCUMENTS

| EP | 0 241 335 A1 | 10/1987 |
| FR | 2 609 868 A1 | 7/1988 |

OTHER PUBLICATIONS

Dudnik et al (2009) : STN International, HCAPLUS database (Columbus, Ohio), Accession No. 2009: 148905.*
Cahiez et al (2008) : STN International, HCAPLUS database (Columbus, Ohio), Accession No. 2008: 881065.*
Alexakis et al., "A New Approach to Conjugated Dienes. Synthesis of the Pheromones of Lobesia Botrana and Bombyx Mori," Tetrahedron, vol. 45, No. 2, 1989, pp. 381-389.
Cahiez et al., "Efficient Preparation of Terminal Conjugated Dienes by Coupling of Dienol Phosphates with Grignard Reagents under Iron Catalysis," Org. Lett., vol. 10, No. 12, 2008 (Published on Web May 14, 2008), pp. 2389-2392, XP-55179257A.
Cahiez et al., "Stereoselective Preparation of Dienol Phosphates from α,β-Ethylenic Aldehydes," J. Org. Chem., vol. 73, No. 17, 2008 (Published on Web Jul. 23, 2008), pp. 6871-6872.
Francke et al., "Female Sex Pheromone of Cameraria ohridella Desch. and Dim. (Lepidoptera: Gracillariidae): Structure Confirmation, Synthesis and Biological Activity of (8E,10Z)-8,10-tetradecadienal and Some Analogues," Z. Naturforsch, vol. 57c, 2002, pp. 739-752.
French Search Report and Written Opinion, dated Apr. 29, 2015, for French Application No. 1456322.
Ideses et al., "Sex Pheromone of European Grapevine Moth (Lobesia botrana) its Chemical Transformations in Sunlight and Heat," Journal of Chemical Ecology, vol. 8, No. 6, 1982, pp. 973-980.
International Search Report (form PCT/ISA/210), dated Sep. 3, 2015, for International Application No. PCT/EP2015/065152.
Khrimian et al., "Syntheses of (Z,E)-5,7-Dodecadienol and (E,Z)-10, 12-Hexadecadienol, Lepidoptera Pheromone Components, via Zinc Reduction of Enyne Precursors. Test of Pheromone Efficacy . . . ", J. Agric. Food Chem., vol. 50, No. 22, 2002 (Published on Web Sep. 26, 2002), pp. 6366-6370.
Leadbetter et al., "An Improved Preparation of Some Insect Sex Attractants: Synthesis and Separation of Geometrical Isomers by Formation of Urea Complexes," Journal of Chemical Ecology, vol. 5, No. 1, 1979, pp. 101-108.
Loreau et al., "Sequential Substitution of 1,2-dichloro-ethene: A Covenient Stereoselective Route to (9Z, 11E)-, (10E,12Z)- and (10Z,12Z)-[1-$^{14}$C] Conjugated Linoleic Acid Isomers," Chemistry and Physics of Lipids, vol. 110, 2001, pp. 57-67.

* cited by examiner

*Primary Examiner* — Golam M Shameem
(74) *Attorney, Agent, or Firm* — Birch, Stewart, Kolasch & Birch, LLP

(57) ABSTRACT

The present invention concerns a method to access (E,Z)-7,9-dodecadienyl-1-acetate in two synthesis steps with excellent yields and selectivity greater than 70% by transformation of 2-hexenal into a novel intermediate, which is itself then transformed into (E,Z)-7,9-dodecandienyl-1-acetate.

9 Claims, No Drawings

METHOD FOR PRODUCING (E,Z)-7,9-DODECADIENYL-1-ACETATE

The present invention concerns a method for obtaining (E,Z)-7,9-dodecadienyl-1-acetate, sex pheromone of the European grapevine moth, or *lobesia botrana*, a grapevine pest lepidoptera. This method is characterized by the use of a novel intermediate 1 defined as a mixture of isomers of the general formula:

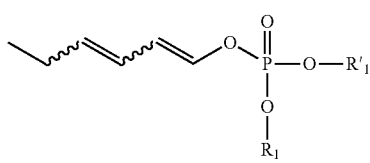

1 where $R_1$ and $R'_1$, identical or different, designate an alkyl or aryl group. These compounds are alkyl-aryl, dialkyl or diaryl-hexa-1,3-dien-1-yl phosphate.

For reasons of public health and management of soil agricultural potential, technologies for treating crops against pests are evolving toward more targeted and environmentally-friendly modes of action. To this end, the use of sex pheromones to change the behavior of insects has advantages since these pheromones are specific to each species of pest and are effective at very low doses, in various strategies (trapping and sexual confusion, for example).

However, development of these technologies is hindered by the cost of access to active molecules. Indeed, these molecules often have many possible isomers and selective synthesis technologies are generally costly.

The primary component of European grapevine moth sex pheromone is (E,Z)-7,9-dodecadienyl-1-acetate. This molecule bears two double bonds and therefore has four possible geometric isomers as seen in the following table:

To effectively respond to the economic problem posed by the synthesis of this pheromone, the following items should be considered:

Only the (E,Z) isomer is active. It is therefore essential to be able to prepare it predominantly. Among all these isomers, the thermodynamically most stable isomer is the (E,E) isomer. It has been shown that when (E,Z)-7,9 dodecadienyl-1-acetate is subject to light exposure or free radical generators, the molecule rearranges into a mixture of these isomers in the proportions of 14/70/14/2 which reflect the equilibrium between these different isomers. (Ideses & al. *Journal of Chemical Ecology*, Vol. 8, No. 1, 1982, p. 973).

It should nevertheless be noted that the three isomers other than (E,Z) are known as not hindering the attractiveness of the pheromone (Ideses & al. *Journal of Chemical Ecology*, Vol. 8, No. 1, 1982, p. 973).

The (E,E) isomer is the most stable isomer and is the main inactive impurity in all known synthesis.

It will therefore be understood that a method for synthesizing the pheromone leading to the very pure active isomer, but at very high production costs, does not respond to the technical and economic problem since a method leading to a lower proportion of the right isomer, but with a good overall yield and a reduced number of synthesis steps, can have a better economic efficiency and thus will allow a better development of the technology of control of the *lobesia botrana* populations in grapevines by sexual confusion.

In order to determine the economic efficiency of a synthesis, it is necessary to consider not only the overall yield of the synthesis which reflects savings in terms of raw material, but also the number of synthesis steps, which governs the cost of implementing said synthesis. By synthesis step, the applicant means any chemistry operation leading to isolating an intermediate. The fewer the number of steps, the more economical the synthesis pathway.

TABLE 1 geometric isomers of 7,9-dodecadienyl-1-acetate

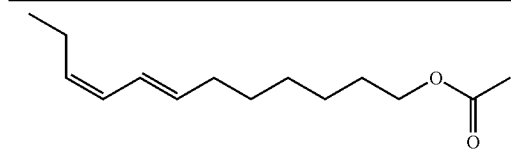

(E,Z)-7,9-dodecadienyl-1-acetate

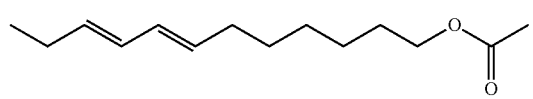 [SMILES: CC/C=C/C=C/CCCCCCOC(C)=O]

(E,E)-7,9-dodecadienyl-1-acetate

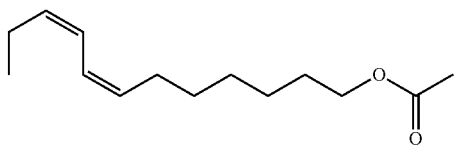 [SMILES: CC/C=C\C=C/CCCCCCOC(C)=O]

(Z,Z)-7,9-dodecadienyl-1-acetate

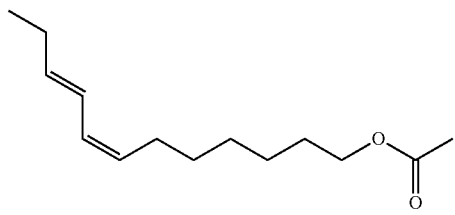 [SMILES: CC/C=C/C=C\CCCCCCOC(C)=O]

(Z,E)-7,9-dodecadienyl-1-acetate

Examination of the solutions proposed in the prior art leads to the following results:

In U.S. Pat. No. 3,954,818 the authors describe a synthesis in more than 9 steps with an unspecified yield and a pheromone purity close to 99%. However, it is necessary to note that this method is difficult to envisage industrially due to the reactants used (lithium wire, butyl lithium, disiamylborane, etc.). The key intermediate of this synthesis is methyl non-4-en-6-ynoate.

In U.S. Pat. No. 3,845,108, the method consists of 8 synthesis steps for an overall yield of 30% from the fourth step and a final purity of only 70%. The method is characterized by an iminophosphonate intermediate and the use of industrially unusable reagents (mercury oxide).

In EP0241335, the authors describe a method in 5 synthesis steps with an overall yield of approximately 10%. The purity of the pheromone is at least 75%. The key intermediate is a 1-halo-(E,Z)-7,9-dodecadiene. This expensive method requires equipment for hydrogenation under pressure. It also uses a Wittig reaction that generates large quantities of triphenyl phosphine that are expensive to eliminate.

U.S. Pat. No. 4,912,253 describes the synthesis of the European grapevine moth pheromone by a coupling catalyzed with copper between a magnesium (chloropentanol derivative) and (E,Z)-2,4-heptadienyl acetate. The preparation of the acetate derivative is difficult, however, and this access pathway, while convergent remains expensive.

In FR2609868, the authors report two synthesis methods for a precursor of a pheromone analog (Z-9-dodecen-9-ynol) via a method characterized in that the key intermediate is an alkynol protected by a tetrahydropyranyl function. The yields are similar to those of EP0241335.

In U.S. Pat. No. 7,932,410, a general method for forming dienes conjugated to a long fatty chain is described, and is characterized by the use of esters with a double bond in the alpha position, such as 1-penten-3-yl isobutyrate which is coupled to a Grignard reagent via a catalyst based on copper complexes. This method is not applicable industrially to the synthesis of (E,Z)-7,9 dodecadienyl-1-acetate since the 1,3-hept-dien-3-yl isobutyrate necessary for this synthesis is very difficult to access industrially.

The conventional synthesis methodologies known in the literature for the synthesis of European grapevine moth pheromone are therefore acetylene intermediates (coupling via acetylides), or coupling reactions between aldehyde and phosphorus ylides called Wittig reactions.

Other more original pathways have also been reported.

In Alexakis & al. Tetrahedron, vol. 45, no. 2, p. 389, 1989, the authors describe an eight-step method that exploits the reactivity of epoxide functions in the presence of silicon derivatives.

In Loreau & al. Chemistry and Physics, 110 (2001) p. 57, a seven-step selective synthesis pathway is described. It has a high cost due to the palladium catalysts that it employs.

In Khrimian & al. Journal of Agric. & Food Chemistry, vol. 50, 22, 2002, p. 6366, the authors develop a fivestep synthesis, but it uses catalysts that cannot be used industrially.

In Franke & al. Znatursforch vol. 57 p. 739 (2002), the authors report a low temperature synthesis pathway using sodium bis (trimethylsilyl) amide which is difficult to extrapolate.

All these synthesis have low yields and have a number of steps that is too large to be easily used industrially. In general, the issues of selectivity are regulated by a post-treatment of the crude reaction via technologies known to those skilled in the art to separate geometric isomers. Examples include chromatography on a silica column impregnated with a silver salt or trapping by Diels Alder reaction of with tetracyanoethylene of E,E compounds or, finally, preferential complexation in a urea matrix of E,E compounds. These additional steps are necessary if the selectivity of the synthesis methods is poor.

This state of the art clearly shows that reducing the number of synthesis steps while maximizing the selectivity for (E,Z)-7,9-dodecadienyl-1-acetate synthesis would make it possible, on the one hand, to save raw materials via a better yield and savings in production costs, reducing the time needed for production.

The applicant has therefore found a novel two-step synthesis method permitting access to (E,Z)-7,9-dodecadienyl-1-acetate with excellent yield and selectivity above 70%.

This novel method is characterized in that it transforms 2-hexenal, an easily accessible product, according to a first step A, into novel intermediate 1, which is itself transformed into crude (E,Z)-7,9-dodecadienyl-1-acetate, via a second step B, according to the following overall synthesis diagram:

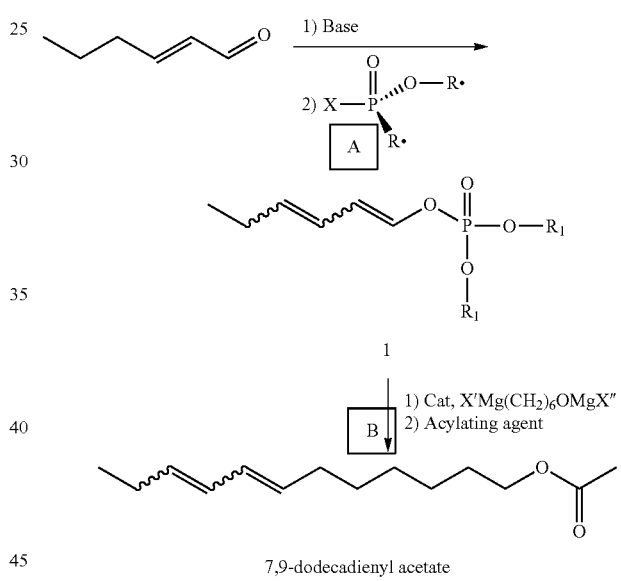

7,9-dodecadienyl acetate and, optionally, (E,Z)-7,9-dodecadienyl-1-acetate is purified by methods known to those skilled in the art.

Thus, the present invention seeks a compound of general formula 1

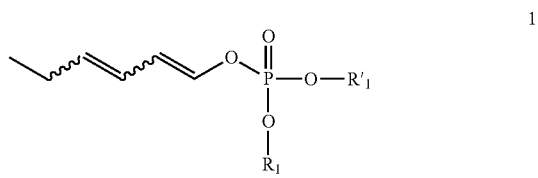

where R1 and R'1, identical or different, designate an alkyl or aryl group.

In one particular embodiment, the invention seeks a compound 1 wherein the alkyl group is chosen from linear or branched C1-C6 alkyls and the aryl group is chosen from among phenyl, benzyl, mesityl or tolyl. The linear or branched C1-C6 alkyl group may be chosen from methyl, ethyl, propyl, isopropyl, butyl, n-butyl, sec-butyl, isobutyl, tert-butyl, pentyl or hexyl.

The invention also concerns the use of a compound 1 according to the invention for the synthesis of compounds containing a conjugated diene unit of the type:

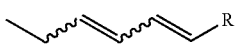

where R represents the radical of the compound onto whom the conjugated diene unit is grafted. The radical R of the compound onto which the conjugated diene unit is grafted can be of various natures, hydrocarbon or carbon-containing, for example, and generally any radical or unit onto which one wishes to graft the above conjugated diene unit in question.

Preferentially, the present invention concerns the use of a compound 1 according to the present invention for the synthesis of pheromones comprising at least one conjugated radical of the formula:

According to a particular embodiment, the invention concerns the use of a compound 1 according to the invention as intermediate for the synthesis of (E,Z)-7,9-dodecenyl acetate.

Thus, one object of the present invention, i.e., step A discussed above, concerns a method for preparation of compound 1 comprising:
  provision of 2-hexenal in an appropriate solvent S1,
  addition of a weakly nucleophilic strong base at a temperature T1 comprised between −78° C. and 25° C. in order to form enolate,
  addition, at a temperature T2, identical to or different from T1, comprised between −78° C. and 25° C., of a halophosphate of formula

where X is a halogen and R1 and R'1 designate identical or different groups chosen from among a linear or branched C1-C6 alkyl, an aryl such as phenyl, benzyl, mesityl or tolyl,
  the recovery of compound 1 after washing and drying of the organic phase.

The method for preparation of compound 1 according to the invention, is more precisely described by the following protocol:
a) One equivalent of 2-hexenal diluted in 2 to 60 volumes of solvent or of a mixture of solvents S1 is prepared in a stirred reactor. The temperature of the reaction medium is brought to a temperature T1 comprised between −78° C. and 25° C., and then 1 to 2 equivalents of a weakly nucleophilic strong base such as an encumbered alkoxide, an encumbered amide or an amidine are added.
b) The alkyl or aryl halophosphate of the following general formula is then added to the reaction medium at a temperature T2 comprised between −78° C. and 25° C., optionally identical to T1:

where R1, R'1, identical or different, are linear or branched C1-C6 alkyl or aryl groups and X a halogen atom, preferably chlorine. The halophosphate is added in an amount of 1 to 2 equivalents relative to 2-hexenal. The linear or branched C1-C6 alkyl group may be chosen from methyl, ethyl, propyl, isopropyl, butyl, n-butyl, sec-butyl, isobutyl, tert-butyl, pentyl or hexyl. The aryl group is chosen from among phenyl, benzyl, mesityl or tolyl.

It is stirred at temperature T2 until compound 1 is formed.

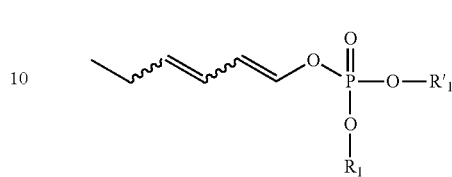

This product is actually a mixture of geometric isomers (E,E), (E,Z), (Z,E) and (Z,Z), whose isomer ratio determines that of the entire method.

In a preferred embodiment, the method for synthesizing compound 1 according to the invention is characterized in that solvent S1 is chosen from the group consisting of tetrahydrofuran (THF), methyl tetrahydrofuran (MeTHF), tetramethylethylenediamine (TMEDA), tetrahydropyran, dimethoxyethane (DME), diethyl ether, methyl tert-butyl ether (MTBE), highly polar nitrogen-containing solvents such as dimethylformamide (DMF), N-methylpyrrolidinone (NMP), N,N'-dimethyl propylene urea (DMPU), methylcyclohexane (MeCy), alkanes of fewer than 8 carbon atoms, aromatic solvents such as toluene and mixtures thereof. Appropriate mixtures are THF/NMP, THF/DMF, THF/DMPU, THF/TMEDA, MTBE/NMP, MeCy/NMP, for example.

According to a particular variant of the invention, the synthesis method for compound 1 described here is characterized in that temperatures T1 and T2, identical or different, are comprised between −40° C. and 15° C.

Even more particularly, the synthesis method for compound 1 according to the invention is characterized in that temperatures T1 and T2, identical or different, are comprised between −20° C. and 0° C.

The synthesis method for compound 1 according to the present invention is characterized in that the weakly nucleophilic strong base is chosen from the group consisting of sodium or potassium terbutanolate, sodium or potassium diisopropylamide, sodium or potassium hexamethyldisilyl azane, 1,5-diazabicyclo[4.3.0]non-5-ene (DBN), or 1,8-diazabicyclo[5.4.0]undec-7-ene (DBU).

Aqueous treatment of the organic solution serves to eliminate certain solvents contained in S1 before the metal coupling implemented subsequently, as well as the salts formed by this step and the excess reagents.

The solution obtained is therefore a solution of compound 1 in a solvent or mixture of solvents S2. The organic phase is dried to be directly used then according to step B mentioned above or evaporated under reduced pressure to isolate intermediate 1.

Also, the present invention concerns a method for preparation of (E,Z)-7,9-dodecadienyl-1-acetate, representing step B indicated above, comprising the following steps:
  provision of product 1 in a solvent S2,
  addition of a catalytic system containing at least one iron atom at oxidation degree III,
  addition, at a temperature T3 comprised between −20° and 60° C., of the compound of general formula X'Mg—(CH$_2$)$_6$—OMgX" where X' and X", identical or different, designate a halogen atom,
  addition of an acetylation agent,
  recovery of (E,Z)-7,9-dodecadienyl-1-acetate after washing and evaporation of organic solvents.

In one particular embodiment, the method for preparing (E,Z)-7,9-dodecadienyl-1-acetate is characterized in that solvent S2 is chosen from the group consisting of THF, MeTHF, MeCy, diethyl ether, methyl tert-butyl ether (MTBE), 1,2-dimethoxyethane and mixtures thereof. Preferably, S2 is a mixture of ethers or alkanes and still more preferentially, S2 is chosen from the group consisting of THF, MeCy, MTBE and MeTHF.

In one preferential embodiment, the preparation method for 7,9-dodecandienyl-1-acetate according to the present invention is characterized in that temperature T3 is comprised between 0° C. and 60° C., particularly between 0° C. and 30° C.

The method for preparing (E,Z)-7,9-dodecadienyl-1-acetate according to the present invention is characterized in that the catalytic system Cat is chosen from the group consisting of iron trihalides, iron triacetate, iron tris-acetylacetonate, iron (III) nitrate, iron (III) phosphate optionally in the presence of ligands chosen from phosphorus or nitrogen-containing ligands.

In one particular embodiment of the method according to the present invention, the acetylation agent is chosen from among the group made up of acetoyl halides, acetic anhydride and alkyl acetate.

The preparation method for (E,Z)-7,9-dodecandienyl-1-acetate according to the present invention, i.e., step B such as indicated above, is more precisely detailed below.

a) The solution of compound 1 in S2 is put in the presence of 0.5 mol % to 2 mol % of a catalytic system Cat that contains an iron atom of oxidation degree III. The mixture is kept stirred, at a temperature T3 comprised between −20° and 60° C., particularly between −5° C. and 25° C. Then a solution of solvent S3 containing the compound of general formula X'Mg—(CH$_2$)$_6$—OMgX" is added, where X' and X", identical or different, designate a halogen atom, particularly a chlorine Cl or bromine Br atom, in an amount of 0.95 to 1.5 equivalents relative to hexenal. The reaction leads to a solution of (E,Z)-7,9-dodecadienolate.

b) Then an acetylation reactant is added, such as acetoyl halides, acetic anhydride or alkyl acetate in an amount of 1.5 to 5 equivalents.

c) The reaction medium is then washed with an aqueous acid solution at a pH comprised between 2 and 6 then with a solution at a pH comprised between 7 and 9. The organic phase is recovered and then concentrated under vacuum to recover crude (E,Z)-7,9-dodecadienyl-1-acetate.

Depending on the purity required, the (E,Z)-7,9-dodecadienyl-1-acetate can be purified. The product purification is done by vacuum distillation.

In one particular embodiment, solvent S3 of the general formula X'Mg—(CH$_2$)$_6$—OMgX" can be chosen from among the group consisting of THF, MeTHF and mixtures thereof.

It is possible to press the purification further by using a method of the art to reduce the extent of the (E,E) isomer. For example, by using the preferential complexation of this isomer in a urea matrix (see Leadbetter & al. Journal of Chemical Ecology, Vol. 5, No. 1, 1979 p. 101) or by preferential reaction with tetracyanoethylene.

In one variant of the method, it is possible chain step A and step B without isolating intermediate 1 which reduces the costs of implementing the procedure even more.

The present invention also concerns a preparation method for 7,9-dodecadienyl-1-acetate, in particular (E,Z) 7,9-dodecanienyl-1-acetate, from 2-hexenal by the succession of steps A and B.

With this method, the applicant obtains much better yields and production cycle times than everything known to those skilled in the art.

Magnesium transfers catalyzed by metals on phosphate enols implemented in step B of the method are described in the literature (see Cahiez & al. in *J. Org. Chem.* 2008, 73, 6871 and *Org. Lett.*, Vol. 10, No. 12, 2008, 2389).

Moreover, it appears that compound 1 is a novel chemical compound easily accessible from 2-hexenal that permits accessing the main component of the European grapevine moth pheromone in a single step.

Reading the work of Cahiez also shows that these reactions are very selective when the initial aldehyde is 2-butenal or 2-pentenal, but that this selectivity is lost for a number of carbon atoms higher than 5. It is therefore not obvious that an aldehyde with 6 carbon atoms leads to a type 1 intermediate with good selectivity (>80%).

Just as the novel compound 1 permits accessing (E,Z)-7,9-dodecadienyl-acetate, it also permits accessing diene derivatives of the general

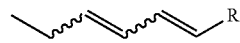

where R represents the radical of the compound onto which the conjugated diene unit is grafted, for example a hydrocarbon or carbon-containing radical or unit onto which one might want to graft said conjugated diene unit.

EXAMPLES

The raw materials and solvents are raw materials available commercially from Sigma Aldrich.

The analytical method consists of gas chromatography (GC) analysis on a HP 5890 Series II device equipped with a FID detector. The chromatographic column is an Innowax 30 m, 0.25 mm, 0.25 μm column with helium as the vector gas.

The furnace follows the following temperature profile: T0=150° C., Initial time 10 min. Gradient 20°/min; Final temperature: 200° C. Duration 7 min.

The injector is at 250° C., the detector at 300° C.

The volume injected is 1 μL. The concentration of the sample is 4 g/L in ethyl acetate (EtOAc).

The reactions are performed in a 2 L double-walled glass reactor provided with a low-temperature cooling system and the distillations are performed by means of a 10 theoretical-plate glass column.

Example 1: Preparation of the Key Intermediate with R1 and R'1=Ethyl

In a reactor provided with stirring, 50 g (0.51 moles) of 2-hexenal diluted in 10 volumes of a 3-2 mixture of THF and NMP (S1) are prepared, the reaction medium temperature is lowered to a temperature T1 of −15° C., and then 69 g (0.61 moles) of potassium tert-butoxide are added. At the end of one hour, at temperature T2, still −15° C., 97 g (0.56 moles) of diethyl chlorophosphate are added. The reaction is stirred for one hour and then the product formed is isolated by washing with a sodium hydroxide solution that permits obtaining 500 g of a solution of enol phosphate in THF. The solution is dried on MgSO$_4$ until the residual water content is less than 0.1%, the content in enol phosphate is assayed by gas chromatography. This solution may be used as such in the following examples.

Compound 1 is isolated by evaporation of the solvents under partial vacuum. 105 g of diethyl-hexa-1,3-dien-1-yl phosphate are recovered in the form of a mixture of two isomers in the following ratio:

Z,Z-diethyl-hexa-1,3-dien-1-yl phosphate: <1%
Z,E-diethyl-hexa-1,3-dien-1-yl phosphate: <1%
E,Z-diethyl-hexa-1,3-dien-1-yl phosphate: 72%
E,E-diethyl-hexa-1,3-dien-1-yl phosphate: 27%

Characterization:
Retention time by gas chromatography: Z,Z-diethyl-hexa-1,3-dien-1-yl phosphate: 13.96 min; Z,E-diethyl-hexa-1,3-dien-1-yl phosphate: 14.27 min; E,Z-diethyl-hexa-1,3-dien-1-yl phosphate: 14.43 min; E,E-diethyl-hexa-1,3-dien-1-yl phosphate: 15.27 min.

RMN $^1$H ($\delta$ ppm, $CDCl_3$): 6.65 (1H, doublet of doublet, CH); 6.26 (1H, triplet, CH); 5.79 (1H, triplet, CH); 5.4 (1H, doublet of triplets), 4.15 (4H, triplet, $OCH_2$), 2.11 (2H, multiplet, $CH_3CH_2$), 1.33 (6H, triplet, $CH_3CH_2O$), 0.97 (3H, triplet, $CH_3CH_2CH$).

Example 2: Synthesis of (E,Z) 7,9-Dodecadienyl-1-Acetate 1.8 g (5.1) mmol of iron tri(acetylacetonate) are added to the intermediate solution of Example 1 and then 0.61 moles of BrMg—$(CH_2)_6$—OMgBr in solution at 1.6 mol/L in MeTHF are poured gently into the reactor. During this addition, the reaction medium is kept at temperature T3 of 25° C. After two hours, 260 g of acetic anhydride are added to the reaction medium, which is now kept stirred at room temperature, until total conversion of the alkoxide formed during iron coupling.

The reaction medium is then washed with a 0.01 molar hydrochloric acid solution, and then with a sodium carbonate solution at a pH of 8. The organic phase is recovered and then concentrated under vacuum to recover crude 7,9-dodecadienyl-1-acetate (88 g assayed at 90% chemical purity and in an E,Z/Z,Z isomer ratio of 76%). I.e., a crude yield of 69% relative to hexenal.

The crude is distilled under high vacuum to give 75 g of 7,9-dodecadienyl-1-acetate with 98% chemical purity and an E,Z isomer content of 76%. I.e., a yield of 66% relative to hexenal.

Enrichment in E,Z Isomer:

The 75 g obtained are mixed with 130 g of urea in 800 ml of methanol. The mixture is left to rest for 3 hours. The suspension is filtered and the residue is washed twice with 100 ml of diethyl ether. The washing fractions are collected with the filtrate and then evaporated under low pressure until complete evaporation of the solvents. 61 g of 7,9-dodecadienyl-1-acetate are obtained, of a chemical purity of 98% and with a content of 90% E,Z isomer.

Examples 3 to 20

In all of the following examples, the experimental protocol of Examples 1 and 2 is used, varying the following parameters:

S1: hexenal dilution solvent.
S2: diethyl-hexa-1,3-dien-1-yl-phosphate dilution solvent.
S3: magnesium compound dilution solvent
X': halide of compound X'Mg—$(CH_2)_6$—OMgX'
T1: hexenal deprotonation temperature
T2: diethyl-hexa-1,3-dien-1-yl-phosphate synthesis temperature
T3: organomagnesium coupling temperature
N1=number of moles of potassium terbutanolate/number of moles hexenal
N2=number of moles of diethyl chlorophosphate/number of moles of hexenal
N3=number of moles of magnesium/number of moles of hexenal The parameters varying in the examples are summarized in Table 1

| Example | S1* | S2 | S3 | X' | T1 | T2 | T3 | N2 (mol) | N4 (mol) | N4 (mol) |
|---|---|---|---|---|---|---|---|---|---|---|
| 3 | THF/NMP (17/12) | THF | THF | Br | −78 | −78 | 0 | 1.2 | 1.1 | 1.2 |
| 4 | THF/NMP (36/12) | THF | MeTHF | Br | −70 | −78 | 0 | 1.2 | 1.2 | 1.2 |
| 5 | THF/NMP (36/17) | THF | MeTHF | Br | −55 | −78 | 0 | 1.1 | 1.1 | 1.2 |
| 6 | THF/DMPU (36/17) | THF | MeTHF | Br | −35 | −78 | 0 | 1.2 | 1.1 | 1.2 |
| 7 | THF/NMP (36/17) | THF | MeTHF | Br | −25 | 0 | 25 | 1.2 | 1.1 | 1.2 |
| 8 | THF/NMP (36/17) | THF | MeTHF | Br | −15 | 0 | 0 | 1.2 | 1.1 | 1.2 |
| 9 | THF/NMP (36/17) | THF | MeTHF | Br | −15 | −15 | 0 | 1.2 | 1.1 | 1.2 |
| 10 | THF/DMPU (36/17) | THF | MeTHF | Br | −15 | −15 | 0 | 1.2 | 1.1 | 1.2 |
| 11 | THF/TMEDA (36/17) | THF | MeTHF | Br | −15 | −15 | 0 | 1.2 | 1.1 | 1.2 |
| 12 | THF/NMP (36/17) | THF | MeTHF | Br | −15 | −10 | 0 | 1.2 | 1.1 | 1.2 |
| 13 | THF/NMP (36/17) | THF | MeTHF | Br | −15 | 0 | 0 | 1.2 | 1.1 | 1.2 |
| 14 | MTBE/NMP (36/17) | MTBE | MeTHF | Br | −15 | −15 | 25 | 1.2 | 1.1 | 1.2 |
| 15 | MeCy/NMP (36/17) | MeCy | MeTHF | Br | −15 | −15 | 0 | 1.2 | 1.1 | 1.2 |
| 16 | MeCy/NMP (10/2) | MeCy | MeTHF | Br | −15 | −15 | 25 | 1.2 | 1.1 | 1.2 |
| 17 | THF/DMF (36/12) | THF | MeTHF | Br | −15 | −15 | 25 | 1.2 | 1.1 | 1.2 |

-continued

| Example | S1* | S2 | S3 | X' | T1 | T2 | T3 | N2 (mol) | N4 (mol) | N4 (mol) |
|---|---|---|---|---|---|---|---|---|---|---|
| 18 | DMF/NMP (14/2) | THF | MeTHF | Br | −15 | −15 | 30 | 1.2 | 1.1 | 1.2 |
| 19 | DMF/NMP (14/2) | THF | THF | Br | −15 | −15 | 25 | 1.2 | 1.1 | 1.2 |
| 20 | DMPU/NMP (14/2) | THF | THF | Br | −10 | −10 | 20 | 1.2 | 1.1 | 1.2 |
| 21 | DMPU/NMP (2/2) | THF | THF | Br | −10 | −10 | 25 | 1.2 | 1.1 | 1.2 |
| 22 | NMP 5V | THF | THF |  | −5 | −5 | 25 | 1.2 | 1.1 | 1.2 |
| 23 | NMP 5V | THF | THF |  | −5 | 0 | 25 | 1.2 | 1.1 | 1.2 |

*the solvent mixture is indicated: the figures in parentheses designate the respective volumes of solvent components relative to hexenal.

The crude yield ($C_Y$) of each example reflects the crude molar yield before distillation.

The $C_{Y(E,Z)}$ ratio designates the proportion of E,Z isomer relative to E,E isomer.

The $C_Y$ and $C_{Y(E,Z)}$ data respectively designate the molar yield and the proportion of E,Z isomer relative to E,E isomer after the purification step.

These results for each example are summarized in Table 2:

| Example | Yc (%) | Yc$_{(E,Z)}$ (%) | Yield (%) | Yield$_{(E,Z)}$ (%) |
|---|---|---|---|---|
| 3 | 63 | 80 | 61 | 85 |
| 4 | 62 | 80 | 60 | 85 |
| 5 | 59 | 79 | 50 | 86 |
| 6 | 61 | 74 | 51 | 86 |
| 7 | 59 | 77 | 51 | 82 |
| 8 | 61 | 74 | 52 | 81 |
| 9 | 59 | 74 | 49 | 81 |
| 10 | 49 | 57 | ** | ** |
| 11 | 42 | 66 | ** | ** |
| 12 | 59 | 74 | 24 | 91 |
| 13 | 44 | 63 | ** | ** |
| 14 | 51 | 74 | ** | ** |
| 15 | 62 | 74 | 49 | 81 |
| 16 | 44 | 65 | ** | ** |
| 17 | 65 | 74 | 52 | 80 |
| 18 | 14 | 72 | ** | ** |
| 19 | 14 | 72 | ** | ** |
| 20 | 38 | 66 | ** | ** |
| 21 | 38 | 66 | ** | ** |
| 22 | 25 | 57 | ** | ** |
| 23 | 25 | 57 | ** | ** |

** the experiments have not been purified

The invention claimed is:

1. A compound of formula 1

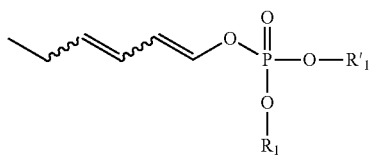

where R1 and R'1, identical or different, designate an alkyl or aryl group,
wherein the compound of formula 1 is an (E,Z) isomer.

2. The compound according to claim 1, wherein the alkyl group is chosen from linear or branched C1-C6 alkyls and the aryl group is chosen from among phenyl, benzyl, mesityl or tolyl.

3. A method for synthesis of (E,Z)-7,9-dodecadienyl-1-acetate, said method comprising:
providing, as an intermediate, a compound 1 according to claim 1 in a solvent;
adding a catalytic system containing at least one iron atom at oxidation degree III;
adding, at a temperature T3 comprised between −20° C. and 60° C., a compound of the formula X'Mg—(CH$_2$)$_6$—OMgX" where X' and X" are identical or different and designate a halogen atom;
adding an acetylation agent; and
recovering (E,Z)-7,9-dodecadienyl-1-acetate after washing and evaporation.

4. The method according to claim 3, wherein the solvent includes at least THF, MeTHF, methylcyclohexane (MeCy), diethyl ether, methyl tert-butyl ether, 1,2-dimethoxyethane or mixtures thereof.

5. The method according to claim 3, wherein the temperature T3 is comprised between 0° C. and 30° C.

6. The method according to claim 3, wherein the catalytic system includes iron trihalides, iron triacetate, iron tris-aceytlacetonate, iron (III) nitrate, or iron (III) phosphate.

7. The method according to claim 6, wherein the iron trihalides, iron triacetate, iron tris-aceytlacetonate, iron (III) nitrate, or iron (III) phosphate is in the presence of ligands chosen from phosphorus or nitrogen ligands.

8. The method according to claim 6, wherein the catalytic system is present at 0.5 mol % to 2 mol % with respect to the solvent and compound of formula 1, wherein the temperature T3 is between −5° C. and 25° C., wherein X' and X" are each a chlorine or bromine atom, wherein the acetylation agent is acetoyl halides, acetic anhydride or alkyl acetate, and wherein the washing is performed with an aqueous acid solution at a pH between 2 and 6 then with a solution at a pH between 7 and 9.

9. A composition including at least 70% of the E,Z isomer of the compound of claim 1.

* * * * *